United States Patent
Slager et al.

(10) Patent No.: US 8,709,489 B2
(45) Date of Patent: Apr. 29, 2014

(54) EMULSIONS CONTAINING ARYLBORONIC ACIDS AND MEDICAL ARTICLES MADE THEREFROM

(75) Inventors: Joram Slager, St. Louis Park, MN (US); Aleksey V. Kurdyumov, Maplewood, MN (US); Dale G. Swan, St. Louis Park, MN (US)

(73) Assignee: SurModics, Inc., Eden Prairie, MN (US)

( * ) Notice: Subject to any disclaimer, the term of this patent is extended or adjusted under 35 U.S.C. 154(b) by 339 days.

(21) Appl. No.: 12/894,983

(22) Filed: Sep. 30, 2010

(65) Prior Publication Data

US 2011/0076337 A1 Mar. 31, 2011

Related U.S. Application Data

(60) Provisional application No. 61/247,408, filed on Sep. 30, 2009.

(51) Int. Cl.
*A61K 9/16* (2006.01)
*A61K 9/50* (2006.01)
*A01K 25/00* (2006.01)
*A61K 47/00* (2006.01)

(52) U.S. Cl.
USPC .......................................... 424/493; 514/777

(58) Field of Classification Search
CPC ... A61K 9/0019; A61K 9/0024; A61K 9/107; A61K 9/113; A61K 9/5036
USPC .......................................... 424/493; 514/777
See application file for complete search history.

(56) References Cited

U.S. PATENT DOCUMENTS

| | | | |
|---|---|---|---|
| 4,093,709 A * | 6/1978 | Choi et al. ................... | 424/424 |
| 5,466,729 A | 11/1995 | Guillet et al. | |
| 5,948,855 A * | 9/1999 | Lin et al. .................... | 524/837 |
| 6,713,558 B2 | 3/2004 | Altes et al. | |
| 6,790,903 B1 | 9/2004 | Majolo et al. | |
| 6,831,128 B2 | 12/2004 | Altes et al. | |
| 6,919,100 B2 | 7/2005 | Narayanan | |
| 7,037,905 B2 * | 5/2006 | Ebdrup et al. .................. | 514/64 |
| 7,060,788 B2 | 6/2006 | Hucks et al. | |
| 7,176,255 B2 | 2/2007 | Mathauer et al. | |
| 7,255,982 B1 * | 8/2007 | Chen-Ho et al. ............. | 430/350 |
| 2003/0100792 A1 * | 5/2003 | Koch et al. ................... | 562/7 |
| 2006/0235370 A1 | 10/2006 | Oblong et al. ................ | 606/9 |
| 2007/0260054 A1 * | 11/2007 | Chudzik .................. | 536/123.12 |
| 2008/0038354 A1 * | 2/2008 | Slager et al. ................. | 424/487 |
| 2008/0125541 A1 | 5/2008 | Hattemer et al. | |
| 2008/0138386 A1 | 6/2008 | Joffre et al. | |
| 2009/0093550 A1 * | 4/2009 | Rolfes et al. ............... | 514/772.7 |
| 2010/0303879 A1 * | 12/2010 | Kurdyumov et al. ......... | 424/422 |
| 2010/0316687 A1 * | 12/2010 | Swan et al. .................. | 424/422 |

FOREIGN PATENT DOCUMENTS

| | | |
|---|---|---|
| EP | 0 771 855 | 5/1997 |
| EP | 0 821 267 | 1/1998 |
| EP | 1 404 685 | 9/2006 |
| WO | 95/12655 | 5/1995 |
| WO | 96/21716 | 7/1996 |
| WO | 2004/046211 | 6/2004 |
| WO | 2007/072189 | 6/2007 |
| WO | 2007/124132 | 11/2007 |
| WO | 2009/102854 | 8/2009 |

OTHER PUBLICATIONS

Murphy et al. (2007). "One-Pot Synthesis of Arylboronic Acids and Aryl Trifluoroborates by Ir-Catalyzed Borylation of Arenes". Organic Letters, 9(5): 757-760.*

Yang et al. (2001). "Computed-Guided Design in Molecular Recognition: Design and Synthesis of a Glucopyranose Receptor". Angew. Chem. Int. Ed., 40(9): 1714-1717.*

* cited by examiner

*Primary Examiner* — Robert T Crow
*Assistant Examiner* — Doan Phan
(74) *Attorney, Agent, or Firm* — Kagan Binder, PLLC

(57) ABSTRACT

The invention provides emulsion compositions that include a hydrophobic compound and an arylboronic acid. An exemplary emulsion comprises a hydrophobic polymer and a halogenated arylboronic acid. Use of an arylboronic acid provides the emulsion with exceptional stability. The stability provides advantages for the formation of articles formed from the emulsion, including microparticles, as well as other implantable or injectable medical articles having polymeric matrices.

25 Claims, 5 Drawing Sheets

EMULSIONS CONTAINING ARYLBORONIC ACIDS AND MEDICAL ARTICLES MADE THEREFROM

PRIORITY CLAIM

This application claims the benefit of U.S. Provisional Patent Application Ser. No. 61/247,408 filed Sep. 30, 2009, entitled EMULSIONS CONTAINING ARYLBORONIC ACIDS, the disclosure of which is incorporated herein by reference.

TECHNICAL FIELD

The present invention relates to emulsion compositions. The invention also relates to the use of emulsion compositions containing hydrophobic polymers for making medically implantable and injectable articles.

BACKGROUND

A polymer emulsion is the suspension of polymers in a liquid. Typically, the polymers are in the form of micron-sized particles suspended in the liquid.

Coatings and films are commonly formed from polymer emulsions. As the liquid evaporates in the polymer emulsion, the suspended polymer solids come closer together until they touch and combine to form larger chains and eventually a film. Polymer emulsions are well known and widely used in the paint industry.

Polymer emulsions have also been used in the field of implantable and injectable medical technologies. In some cases, polymer emulsions have been used for coating medical devices. It has become appreciated that coatings can improve function of an implanted device at the site of implantation. For example, coatings for implantable medical devices can improve biocompatibility of the device surface, or provide a drug-delivery mechanism. U.S. Pat. No. 6,919,100 describes a process of applying an aqueous latex polymeric emulsion of vinylidenefluoride, hexafluoropropolyene, and an antiproliferative drug, and then drying the aqueous latex polymeric emulsion on the medical device to form a drug-releasing coating.

Polymer emulsions have also been used for the preparation of drug-containing microparticles. Microparticle formation using an emulsion-based process typically begins with the preparation of two separate liquid phases, first and second liquid phases. The first liquid phase is a solution (or dispersion) a drug in a solution of polymer dissolved in a first solvent. The second phase is a solution of surfactant and a second solvent. The second solvent is at least partially immiscible with the first solvent of the first phase. To form the emulsion, the first phase is combined with an excess amount of the second phase, generally using agitation or mixing. Microdroplets of the first phase become dispersed in the second (continuous) phase. The surfactant in the second phase can help to form and stabilize the dispersion of microdroplets in the second phase. The emulsion is then treated so that the polymeric material in the microdroplets hardens to form drug-containing polymeric microparticles. Often, to form the microparticles, the first solvent (which was originally used to dissolve the polymer) is removed by evaporation or extraction.

Unfortunately, emulsions are inherently unstable and undergo many destabilization phenomena, such as coalescence (particles combine to form a layer of liquid), flocculation (particle clumping), and creaming (particles concentrate near the top of bottom of the emulsion). Some of these can lead to phase separation of the materials in the emulsion. Destabilization of emulsions can be due to various causes, such as the type of polymer used, the type or amount of surfactant, and interaction of solid components in the emulsion. While surfactants can be added to stabilize emulsions, some may not be particularly effective or may not stabilize the emulsion for a desired period of time. Also, if the emulsion is used for formation of implantable or injectable material, some surfactants may not be suitable due to insufficient biocompatibility. In turn, destabilization can affect formation of coatings and microparticles. Loss of stability may also affect bioactive agent if included in the microparticles.

SUMMARY OF THE INVENTION

Generally, the present invention relates to emulsion compositions that include a hydrophobic compound, such as a hydrophobic polymer. The emulsion composition also includes a member of a class of compounds that can provide the emulsion with exceptional stability. Through experimental investigations associated with the invention, it has been found that arylboronic acids provide remarkably stability when included in an emulsion comprising a hydrophobic compound. On preferred group of arylboronic acids is halogenated arylboronic acids. Halogenated arylboronic acids include mono- and di-halogenated phenyl boronic acids, such as chlorophenylboronic acid and dichlorophenylboronic acid.

An arylboronic acid, such as a halogenated arylboronic acid, can be present in the organic phase liquid of the emulsion along with the hydrophobic compound (for example, in the continuous phase of an oil-in-water-type of emulsion, or the discontinuous phase of a water-in-oil-type of emulsion). Alternatively, the arylboronic acid can be present in the aqueous phase liquid, such as in a suspension or dispersion.

Reactive chemistries can be present on the hydrophobic compound, such as a hydrophobic polymer, to facilitate formation of solidified three-dimensional structures (for example, microparticles) from the emulsions. In some aspects, the reactive chemistries are provided by moisture-sensitive reactive groups, such as silane-ether containing groups. An emulsion stabilized using an arylboronic acid, such as a halogenated arylboronic acid, and containing particulates including a hydrophobic polymer with a reactive chemistry, can be treated to cause reaction of the reactive groups and crosslinking of the polymers, or reaction of the polymers with a secondary material. For example, polymeric articles such as microparticles and coatings are formed using the stabilized emulsions with hydrophobic polymers including reactive chemistries. The emulsions and methods can be used to form articles for medical use (such as implantable or injectable articles), as well as in other commercial areas.

Therefore, in one embodiment, the invention provides an emulsion comprising a hydrophobic compound and an arylboronic acid, such as a halogenated arylboronic acid.

In some aspects, the hydrophobic compound in the stabilized emulsion is a hydrophobic polymer. The invention contemplates a broad range of polymers having a hydrophobic property, including homopolymers, copolymers, biostable polymers and biodegradable polymers.

In some aspects the stabilized emulsion comprises a silane-containing hydrophobic compound. The silane-containing hydrophobic compound can be a silane-containing hydrophobic polymer. Exemplary polymers comprise pendent silane-containing groups. In some aspects, silane-containing pendent group comprises a reactive group, such as a silyl ether group.

The invention also includes methods for forming a polymeric matrix from the polymer emulsion. The method comprises a step of obtaining a polymer emulsion comprising an arylboronic acid, such as a halogenated arylboronic acid, and a hydrophobic polymer. The method also comprises a step of forming the polymer in the emulsion into a polymeric matrix.

In an exemplary mode of practice, the polymer comprises a reactive silane-containing group that is reacted in the method to form a polymeric matrix. For example, the silane-containing group can be reacted to crosslink the polymer, or to bond the polymer with a secondary material, such as another polymer or the surface of a device. The crosslinked polymeric matrix can include a crosslinker segment with two or more silane groups.

The invention also includes articles formed from the emulsions comprising the hydrophobic polymer and an arylboronic acid, such as a halogenated arylboronic acid. The emulsions can be used to form a medical article, such as an implantable or injectable medical article. Exemplary implantable or injectable medical articles include microparticles and coatings for medical devices.

The emulsions can also include a bioactive agent. These emulsions can be used to form an implantable or injectable medical article that includes bioactive agent, wherein the bioactive agent can be released when the article is introduced into the body.

Use of an arylboronic acid, such as a halogenated arylboronic acid, provides various advantages for methods and articles formed using hydrophobic compounds. For example, the stabilizing effect achieved with the arylboronic acid gives the emulsions an unusually long shelf life which is advantageous for manufacturing, as well as in shipping, and other commercial uses. Further, their remarkable stability dictates that articles formed from these emulsions will be of higher quality, which can enhance use of the formed articles for certain applications. For example, use of the emulsions of the invention can provide articles with improved properties, such as uniformity of size, shape and thickness. When reactive chemistries are used in association with the hydrophobic compound, the stabilized emulsions allows reactions to be carried out over longer periods of time which can result in a well-formed polymeric matrix. The arylboronic acid provides can also enhance the stability of emulsions that include drugs, as well as drug-containing implantable or injectable articles formed from the emulsion and useful for delivering the drug to a subject.

DETAILED DESCRIPTION

Figure 1A:
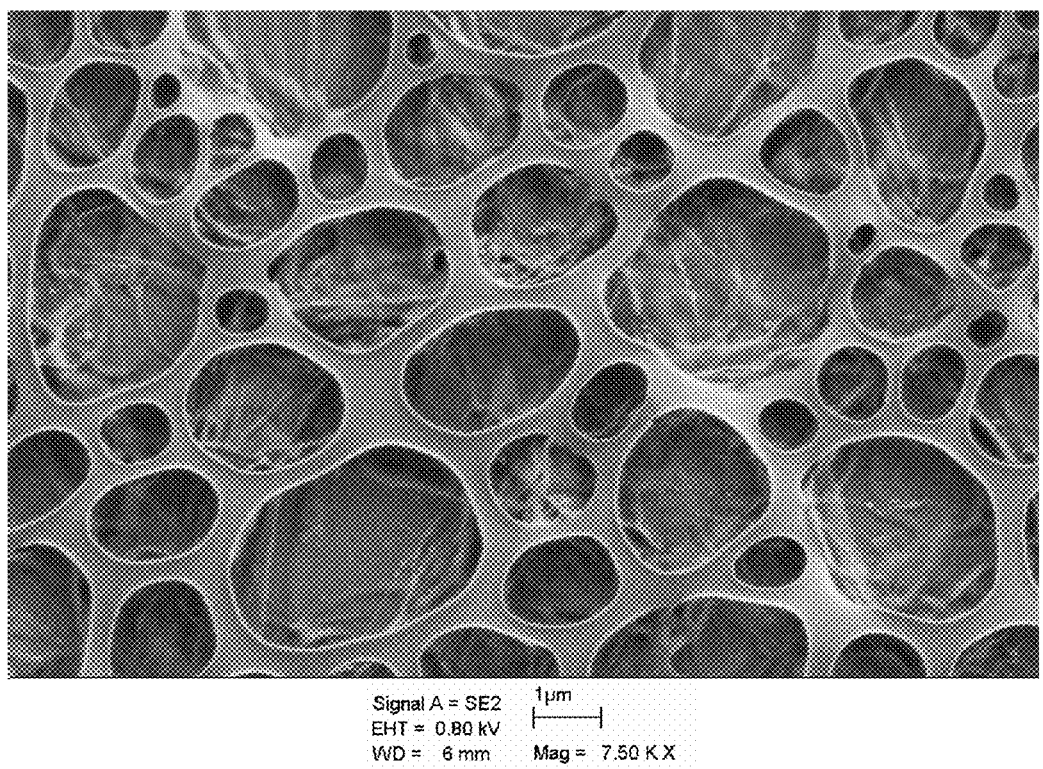
FIGS. 1A-1C are micrographs of air-dried emulsions of silyl ether-modified hydrophobic α(1→4)glucopyranose polymers.

The embodiments of the present invention described herein are not intended to be exhaustive or to limit the invention to the precise forms disclosed in the following detailed description. Rather, the embodiments are chosen and described so that others skilled in the art can appreciate and understand the principles and practices of the present invention.

All publications and patents mentioned herein are hereby incorporated by reference. The publications and patents disclosed herein are provided solely for their disclosure. Nothing herein is to be construed as an admission that the inventors are not entitled to antedate any publication and/or patent, including any publication and/or patent cited herein.

The invention is generally directed to stabilized emulsion compositions comprising a hydrophobic compound and an emulsion stabilizer comprising an arylboronic acid, such as a halogenated arylboronic acid. The invention is also directed to methods for forming articles using the emulsion compositions of the invention, as well as the articles formed from the stabilized emulsions, such as microparticles and coatings.

In more specific aspects, the emulsion compositions comprise one or more of the following features: a hydrophobic polymer, a reactive chemistry attached to the hydrophobic compound (such as a reactive silane ether-containing group). Exemplary emulsion compositions include an arylboronic acid, such as a halogenated arylboronic acid, and a biodegradable hydrophobic polymer comprising pendent reactive silane-containing group.

In one aspect, the emulsion comprises an arylboronic acid. The boronic acid group (or more than one boronic acid group) is attached to the aryl group at a position on the aryl ring. The positions on the aryl ring not occupied by the boronic acid group can be substituted or unsubstituted (—H).

For example, in one aspect, the emulsion composition comprises phenylboronic acid:

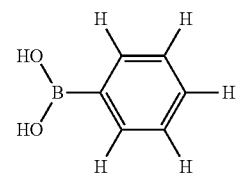

In another aspect, the emulsion comprises a halogenated arylboronic acid. A halogenated arylboronic acid includes one or more of a boronic acid group, and one or more halogen atoms attached to the aryl ring. The boronic acid group and the halogen atom are attached to the aryl (e.g., phenyl) group at positions on the aryl ring.

In another aspect, the emulsion composition comprises a halogenated arylboronic acid according to Formula I:

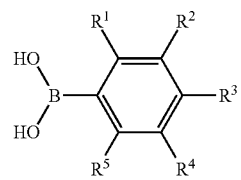

wherein one or more of $R^1$, $R^2$, $R^3$, $R^4$, and/or $R^5$ is/are selected from a halogen atom, and any $R^1$, $R^2$, $R^3$, $R^4$, and/or $R^5$ positions not occupied by a halogen atom are selected from H.

In some aspects the halogen atom is independently selected from F, Cl, Br, and I.

In more specific aspects two of $R^1$, $R^2$, $R^3$, $R^4$, and $R^5$ are independently selected from halogen atoms.

In more specific aspects two of $R^1$, $R^2$, $R^4$, and $R^5$ are independently selected from halogen atoms.

In more specific aspects one or more of $R^1$, $R^2$, $R^3$, $R^4$, and/or $R^5$ are Cl.

In more specific aspects two of $R^1$, $R^2$, $R^3$, $R^4$, and/or $R^5$ are Cl.

In more specific aspects two of $R^1$, $R^2$, $R^4$, and $R^5$ are Cl.

In more specific aspects $R^2$ and $R^4$ are Cl, or $R^3$ and $R^5$ are Cl.

Exemplary chlorinated arylboronic acids include 3,5-dichlorophenylboronic acid, shown below:

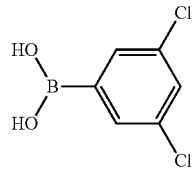 [SMILES: OB(O)c1cc(Cl)cc(Cl)c1]

as well as 2-chlorophenylboronic acid, 3-chlorophenylboronic acid, 4-chlorophenylboronic acid, 2,3-dichlorophenylboronic acid, 2,4-dichlorophenylboronic acid, 2,5-dichlorophenylboronic acid, and 2,6-dichlorophenylboronic acid, and the like. Alternatively, fluorine, bromine, and iodine atoms can be substituted for the chlorine atom(s) at one or more of these positions. The halogenated arylboronic acid can include combinations of different halogen atoms.

Halogenated aryl boronic acids are available from a variety of commercial sources, such as Sigma Aldrich.

The hydrophobic compound that can be included in the emulsion composition along with the arylboronic acid, such as a halogenated arylboronic acid, can be a hydrophobic polymer, or a hydrophobic non-polymeric compound. Exemplary hydrophobic non-polymeric compounds include low molecular weight hydrophobic compounds. Low molecular weight hydrophobic compounds can include biologically active agents (e.g., small organic pharmaceuticals), as well as those having no clear therapeutic application.

As described herein, a "hydrophobic polymer" refers to a substantially water-insoluble polymer. Generally, the water-insolubility of a hydrophobic polymer is maintained throughout the pH range. One or more chemical feature(s) can provide the hydrophobic property of a hydrophobic polymer.

The part or parts of the polymer that provide hydrophobic properties to the silane-containing hydrophobic polymer can be referred to herein as the "hydrophobic portion." The hydrophobic portion can constitute all or a portion of the silane-containing hydrophobic polymer.

In some cases, the hydrophobic property of the hydrophobic polymer can be achieved by virtue of the polymer containing one or more hydrophobic monomer(s) present in the polymer in the polymerized form in an amount or amounts sufficient to render the polymer hydrophobic. In some circumstances, the hydrophobic polymer can include monomers that are not hydrophobic, or that are even hydrophilic in nature, provided that the type(s) and amount(s) of hydrophobic monomer(s) are sufficient to provide an overall hydrophobic property.

The hydrophobic polymer can include one or more groups that are "pendent" from the polymer backbone, referring to those chemical groups that essentially hang off the polymeric backbone. The polymer can have pendent hydrophobic groups, such as ones including hydrocarbon segments, present in an amount to confer hydrophobicity to the polymer. Pendent hydrophobic groups can constitute all or a part of the hydrophobic portion of the polymer. In some modes of practice, pendent groups are formed by grafting onto a polymer backbone, such as by the chemical modification along the length of the polymer. Pendent hydrophobic groups can be used in conjunction with a polymer backbone that is hydrophilic, hydrophobic, or that includes chemistries providing both hydrophilic and hydrophobic properties.

In many aspects the hydrophobic portion comprises one or more hydrocarbon chemistries, and the hydrocarbon chemistries are present in an amount and type sufficient to provide requisite hydrophobicity. For example, the hydrophobic monomers or pendent hydrophobic groups of the polymer include monovalent or divalent hydrocarbon groups. Hydrocarbon groups can contain unsaturated and saturated hydrocarbon groups, and examples thereof include alkyl, alkenyl, alkynyl, cyclic alkyl, cyclic alkenyl, aromatic hydrocarbon and aralkyl groups.

A hydrophobic polymer used in an emulsion of the invention can be defined by its solubility non-aqueous solvent. Hydrophobic polymers generally have property of being soluble in a variety of solvents that are commonly used for dissolving hydrophobic polymers. The solubility of the hydrophobic polymer in a solvent will depend on the particular chemistry or chemistries constituting the polymer, as well as the particular solvent or combination of solvents used. The non-aqueous solvent (or solvents) suitable for dissolution of the hydrophobic polymer can be used for forming one of the phases (e.g., the discontinuous or continuous phase) of the emulsion.

In some aspects, the hydrophobic polymer can include a non-hydrophobic portion. For example, the non-hydrophobic portion can (in itself) display partial or substantial water-soluble properties. However, the hydrophobic portion of the polymer predominates and causes hydrophobicity.

Polymer(s) used for the preparation of an emulsion can have solubility in alcohols (e.g., methanol, ethanol and isopropanol), alkanes (e.g., halogenated or non-halogenated alkanes such as hexane, methylene chloride and chloroform), ethers (e.g., tetrahydrofuran (THF)), ketones (e.g., acetone, methyl ethyl ketone, methyl isobutyl ketone), aromatic compounds (e.g., toluene and xylene), nitriles (e.g., acetonitrile), and ester (e.g., ethyl acetate and butyl acetate).

Within a particular solvent, a hydrophobic polymer used for emulsion preparation may be determined to be soluble (having a solubility of at least 1 part agent per from 10 to 30 parts solvent), freely soluble (having a solubility of at least 1 part agent per from 1 to 10 parts solvent), or very soluble (having a solubility of greater than 1 part agent per 1 part solvent). These descriptive terms for solubility are standard terms used in the art (see, for example, *Remington: The Science and Practice of Pharmacy*, 20th ed. (2000), Lippincott Williams & Wilkins, Baltimore Md.).

In some instances, the polymers as discussed herein can be described in terms of molecular weight. "Molecular weight," as used herein, more specifically refers to the "weight average molecular weight" or $M_w$, which is an absolute method of measuring molecular weight and is particularly useful for measuring the molecular weight of a polymer (preparation). Polymer preparations typically include polymers that individually have minor variations in molecular weight. In some cases, the polymers have a relatively higher molecular weight (e.g., versus smaller organic compounds) and such minor variations within the polymer preparation do not affect the overall properties of the polymer preparation. The weight average molecular weight ($M_w$) can be defined by the following formula:

$$M_w = \frac{\sum_i N_i M_i^2}{\sum_i N_i M_i}$$

wherein N represents the number of moles of a polymer in the sample with a mass of M, and $\Sigma_i$ is the sum of all $N_i M_i$ (species) in a preparation. The $M_w$ can be measured using common techniques, such as light scattering or ultracentrifugation. Discussion of $M_w$ and other terms used to define the molecular weight of polymer preparations can be found in, for example, Allcock, H. R. and Lampe, F. W., *Contemporary Polymer Chemistry*; pg 271 (1990).

Various polymer types can be used in the emulsion composition along with the halogenated arylboronic acid. A hydrophobic polymer used in the emulsion can be based on a homopolymer, or a copolymer.

Generally, a homopolymer is a polymer wherein the repeating monomeric units that form the polymer backbone are identical. Homopolymers can be in linear or branched form. In some aspects, the hydrophobic polymer used in the emulsion comprises a homopolymeric backbone and pendent groups or branches that are different than the polymeric backbone. The pendent groups or branches may confer hydrophobicity to the polymer.

Alternatively, the hydrophobic polymer used in the emulsion can be a copolymer. A copolymer (also "heteropolymer" herein) broadly refers to those polymers that include two or more different monomeric units. Examples include random and non-random (ordered) copolymers. An alternating copolymer includes two or more regularly alternating monomeric units (for example, including dimeric unit -(AB)$_n$—). A copolymer can also be a block copolymer which refers to those including comprise two or more covalently-linked homopolymeric or heteropolymeric subunits (segments). Examples of block copolymers include diblock copolymers (two repeating homopolymer or heteropolymeric subunits) and triblock copolymers (two repeating homopolymer subunits).

A hydrophobic polymer used in the emulsion can be a branched polymer, referring to those polymers having one or more polymeric branches attached to a main polymeric chain (polymeric backbone). The point at where a branched polymer chain is attached to another (e.g., a main) polymer chain is called a branch point. Examples of branched polymers include graft polymers, star polymers, comb polymers, and brush polymers. Homopolymer and/or copolymer chains can form the polymeric branches and the main polymeric chain.

A graft polymer has one or more polymeric branch(es) (attached to the main chain) that are different than the main chain. A star polymer has a single branch point from which two or more linear polymer chains are extended. A comb polymer has a main chain and two polymeric branches on the main chain that are linear polymers.

In some aspects, the hydrophobic polymer used in the emulsion can be a degradable (also "erodible" herein) polymer. Examples of degradable polymers are those that have polymeric backbones with linkages are hydrolyzed by simple hydrolysis conditions, and well as those that have polymeric backbones with linkages that are enzymatically hydrolyzed. A degradable polymer can have a "degradable portion" referring to a part of the polymer capable of erosion, such as by hydrolysis as described. A degradable portion of a degradable polymer can constitute the entire polymer, or one or more portions of the polymer, such as when the polymer includes degradable and non-degradable polymeric blocks. As such, degradable polymers can also have degradable (or erodible) and non-degradable (or non-erodible) portions. For example, hydrophobic polymer can be based on a block copolymer that includes degradable and non-degradable polymeric segments. Generally, all or portions of degradable polymers can break down into their monomeric constituents when implanted or injected into a mammal.

Using the stabilized emulsion, a degradable hydrophobic polymer can be formed into a biodegradable polymeric matrix (e.g., a polymeric matrix in the form of microparticles). The degradable hydrophobic polymer in the polymer emulsion can also be used to form an implantable or injectable article having a polymeric matrix portion that is degradable.

The hydrophobic polymer can be based on a biodegradable polymeric backbone (e.g., main chain) with pendent groups or polymeric branches from the polymeric backbone that are chemically different than the polymeric backbone. A specific example of such a polymer is a silyl ether-modified hydrophobic $\alpha(1\rightarrow 4)$glucopyranose polymer, containing a $\alpha(1\rightarrow 4)$glucopyranose polymeric backbone and pendent hydrophobic and silyl ether-containing groups.

In some aspects the emulsion is prepared with a hydrophobic polysaccharide. The preparation of hydrophobic polysaccharides can be found in, for example, U.S. Patent Application Publication No. 20070260054 (Chudzik et al., Nov. 8, 2007).

Representative hydrophobic polysaccharides include hydrophobic $\alpha(1\rightarrow 4)$glucopyranose polymers which have at least a first portion that is a $\alpha(1\rightarrow 4)$glucopyranose polymeric backbone, and a second portion that is a hydrophobic portion including hydrophobic groups that are pendent from the polymeric backbone. The $\alpha(1\rightarrow 4)$glucopyranose polymeric backbone is representative of the polysaccharide portion of the polymer. The hydrophobic groups can include hydrocarbon groups, such as described herein.

An $\alpha(1\rightarrow 4)$glucopyranose polymer, which forms the poly-$\alpha(1\rightarrow 4)$glucopyranose portion of a hydrophobic $\alpha(1\rightarrow 4)$glucopyranose polymer, includes repeating $\alpha$-D-glucopyranose (Glc$_p$) monomers having $\alpha(1\rightarrow 4)$ linkages. A portion (three monomeric units) of an $\alpha(1\rightarrow 4)$ glucopyranose polymer is shown below:

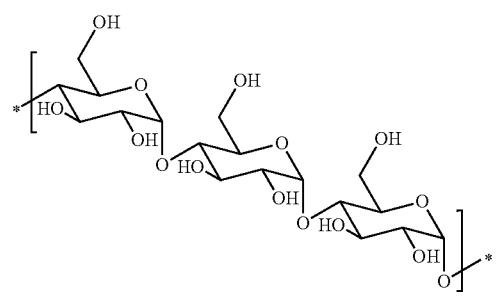

As starting material for the preparation of a hydrophobic $\alpha(1\rightarrow 4)$glucopyranose polymer, one can use $\alpha(1\rightarrow 4)$glucopyranose polymers such as maltodextrin, amylose, cyclodextrin, and polyalditol (polyalditol is available from GPC (Muscatine, Iowa) under the tradename INNOVATOL™ PD60, and has <1% reducing sugars). Maltodextrins generally refer to those polymer preparations having a lower molecular weight than amylose preparations. Cyclodextrins are low molecular weight cyclic $\alpha(1\rightarrow 4)$glucopyranose polymers.

Exemplary maltodextrin and amylose polymers have molecular weights ranging from about 500 Da to about 500,000 Da, about 1000 Da to about 300,000 Da, and about 5000 Da to about 100,000 Da.

Maltodextrin and amylose polymers of various molecular weights are commercially available from a number of different sources. For example, GLUCIDEX™ 6 (ave. molecular weight ~95,000 Da) and GLUCIDEX™ 2 (ave. molecular weight ~300,000 Da) are available from Roquette (France); and MALTRIN™ maltodextrins of various molecular weights, including molecular weights from about 12,000 Da to 15,000 Da are available from GPC (Muscatine, Iowa).

In underivatized form, the glucopyranose units of the α(1→4)glucopyranose polymers include monomeric units having ring structures with primary and secondary hydroxyl groups. Primary and secondary hydroxyl groups can be reacted with hydroxyl reactive compounds to provide hydrophobic groups that are pendent from positions on the glucopyranose monomeric units previously corresponding to either or both primary and/or secondary hydroxyl locations. In forming the hydrophobic α(1→4)glucopyranose polymer, a compound having a hydrophobic group with a hydrocarbon segment can be covalently coupled to one or more portions of an α(1→4)glucopyranose polymer. For example, compounds reactive with the α(1→4) glucopyranose polymers can include a hydroxyl-reactive group such as acetal, carboxyl, anhydride, acid halide, and the like, and a hydrocarbon group.

A pendent hydrophobic group can include a "hydrocarbon segment" which refers to a group of covalently bonded carbon atoms. A hydrocarbon segment can include saturated hydrocarbon groups or unsaturated hydrocarbon groups, and examples thereof include alkyl, alkenyl, alkynyl, cyclic alkyl, cyclic alkenyl, aromatic hydrocarbon and aralkyl groups. A hydrocarbon segment can have the formula —$(CH_n)_m$—$CH_3$, wherein m is 2 or greater, and n is independently 2 or 1. In some cases, two or more hydrocarbon segments can be separated from each other by a non-carbon atom, or a non-carbon-containing group. In some aspects, a pendent hydrophobic group comprises a hydrocarbon segment that is a linear, branched, or cyclic group containing two or more carbon atoms. More preferably the hydrocarbon segment comprises a $C_2$-$C_{15}$-containing, a $C_2$-$C_{10}$-containing, or a $C_4$-$C_8$-containing, linear, branched, or cyclic hydrocarbon group.

In some instances, a hydrolytically-cleavable covalent bond is present between the hydrophobic group and the glucopyranose unit of the polysaccharide backbone. The chemistry of the portion of the polysaccharide derivative between the hydrophobic group and the glucopyranose unit of the polysaccharide backbone can be referred to as the "linker" segment. Cleavable chemical linkages of the linker segment include silyl ether, peroxyester, disulfide, and hydrazone groups. Some chemical linkages, such as ones including urethane bonds, have a slow rate of hydrolysis.

The hydrophobic polymer can be based on an aliphatic polyester, which can be used in the inventive emulsion compositions. The aliphatic polyester can be used to form degradable polymeric articles from the emulsion. The aliphatic polyester can be an aliphatic polyester copolymer, or aliphatic polyester homopolymer. The aliphatic polyester can be based on the polymerization of one or any combination of the following monomers selected from the group consisting of lactide, glycolide, dioxanone, tartronic acid, hydroxyvalerate, hydroxybutyrate, malonic acid, valerolactone, and caprolactone. Specific examples of homo- and copolymers formed from these monomers include, but are not limited to, polylactide, polyglycolide, polycaprolactone, polydioxanone, poly(lactide-co-glycolide), poly(glycolide-co-polydioxanone), and poly(glycolide-co-caprolactone).

Alternatively, a hydrophobic polymer used in the emulsion can be a non-erodible or non-degradable polymer. Examples of non-erodible or non-degradable polymers are those that have polymeric backbones with linkages that are not hydrolyzed by simple hydrolysis conditions, or those that have polymeric backbones with linkages that are not enzymatically hydrolyzed. Generally, non-erodible or non-degradable polymers do not break down into their monomeric constituents when implanted or injected into a mammal. Non-erodible or non-degradable polymers that are used for an injectable emulsion or when the emulsion is used to form an injectable or implantable article are generally biocompatible, meaning that they do not have an adverse affect (e.g., are toxic) when introduced into on the body.

Exemplary non-degradable polymers include those that are acrylate-based. The hydrophobic polymer can be based on a poly(alkyl-acrylate) or poly(aromatic acrylate) polymer, and can be used in the inventive emulsion compositions. As used herein, poly(alkyl-acrylate) and poly(aromatic acrylate) polymers, refers to the polymer in either the acrylic and/or methacrylic form (corresponding to the acrylates and/or methacrylates, respectively). Poly(alkyl acrylates) and poly (aromatic acrylates), if not copolymerized with other monomers or pre-polymer that provide degradable linkages in the polymer backbone, are generally non-degradable polymers.

Examples of poly(alkyl acrylates) include those with alkyl chain lengths from 2 to 8 carbons. Specific examples of poly (alkyl acrylates) are poly(n-butyl methacrylate) and poly(t-butyl methacrylate). Examples of (alkyl acrylate) copolymers include poly(n-butyl methacrylate-co-methyl methacrylate) and poly(n-butyl methacrylate-co-isobutyl methacrylate). Examples of poly(aromatic acrylates) include poly(aryl acrylates), poly(aralkyl acrylates), poly(alkaryl acrylates), poly (aryloxyalkyl acrylates), and poly(alkoxyaryl acrylates).

In some aspects, a hydrophobic polymer used in the emulsion includes a reactive chemistry. The reactive chemistry can be used to facilitate formation of a polymeric matrix from the stabilized polymeric emulsion. For example, the reactive chemistry can be used to form covalent bonds that crosslink the hydrophobic polymer to form a polymeric matrix. The reactive chemistry can also be used to form covalent bonds that attach the hydrophobic polymer to a secondary article, such as another (e.g., secondary) polymeric material or to a surface of a device. Reactive chemistries include thermochemically-reactive groups (such as nucleophilic/electrophilic pairs), latent reactive groups that are activated by light (photoreactive) or by heat, moisture-sensitive reactive chemistries that undergo condensation reactions, and free-radical polymerizable groups.

In some aspects, the hydrophobic polymer comprises a silane-containing group. A silane-containing group can include a silyl ether group. Generally, a "silyl ether group" includes a silicon atom bonded to one or more carbon-containing groups via an oxygen atom (i.e., an ether linkage).

Exemplary silane-containing groups include reactive silane ether groups which are moisture sensitive and can undergo a condensation reaction to form covalent bonds to provide polymer-polymer crosslinking or bonding of the polymer to a secondary material. Exemplary carbon-containing groups that can form a portion of the silyl ether group include covalently bonded carbon atoms having the formula —$(CH_2)_m CH_3$, wherein m is 0 or an integer in the range of 1 to 5.

In some aspects, the emulsion includes a silyl ether group on a hydrophobic polymer having formula II:

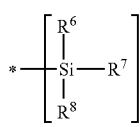

The silyl ether group can be pendent from one or more monomeric units of the polymer backbone.

In formula II, $R^6$, $R^7$, and $R^8$ are independently selected from $R^9$ and $OR^9$, wherein $R^9$ includes a hydrocarbon group, such as a C1-C6-containing hydrocarbon group, or more specifically a linear or branched C1-C6 alkyl group, with the proviso that at least one $R^6$, $R^7$, or $R^8$ is $OR^9$. For example, in some more specific aspects of formula I, one of $R^6$, $R^7$, or $R^8$ is $OR^9$, wherein $R^9$ is a hydrocarbon group, such as a C1-C6-containing hydrocarbon group, and the other groups that are not $OR^9$ are independently selected from $R^9$.

In other specific aspects of formula II, all of $R^6$, $R^7$, and $R^8$ are independently selected from $OR^9$, wherein $R^9$ is a C1-C6-containing hydrocarbon group.

Exemplary carbon-containing groups include a group of covalently bonded carbon atoms having the formula $-(CH_2)_m CH_3$, wherein m is 0 or an integer in the range of 1 to 5. Exemplary $R^9$ groups include methyl, ethyl, propyl, isopropyl, n-butyl, isobutyl, and t-butyl.

A silane-containing group can be attached to a hydrophobic polymer using reactive chemistries. In another mode of synthesis, a polymer having a silane-containing group is obtained, and then the polymer is further derivatized to add hydrophobic groups.

Various silane-containing compounds reactive with a portion of a polymer can be used to prepare a silane-containing hydrophobic polymer. For example, a polymer may provide one or more groups such as hydroxyl, amine, and/or carboxylate along its length, or at (a) terminus/termini. These groups can be reactive with a silane-containing compound also having a hydroxyl, amine, and/or carboxylate-reactive group, such as epoxide, N-oxysuccinimide, aldehyde, isothiocyanate, anhydride, hydrazide, isocyanate, and maleimide. Various hydroxyl, amine, and/or carboxylate-reactive silane-containing compounds are available from Sigma Aldrich, such as (3-glycidyloxypropyl)trimethoxysilane and 3-(triethoxysilyl)propyl isocyanate.

As another example for preparation of the polymer, silane-containing monomers can be polymerized in a free radical polymerization reaction to provide a silane-containing polymer. The silane-containing monomers can be polymerized in an amount to provide a desired molar/weight quantity of silane in the polymer. Other monomer types can be chosen to provide a silane-containing copolymer with properties as desired, such a degradability or non-degradability, flexibility, etc. The monomers can have chemistries so the silane group is presented as pendent from the polymer backbone. Various free-radical polymerizable silane-containing monomers are available from Sigma Aldrich, such as trimethoxy(7-octen-1-yl)silane.

Silane functionalized hydrophobic polysaccharides including a silyl ether group according to formula II are described in commonly assigned U.S. Provisional Patent Application No. 61/217,625 (Kurdyumov et al., filed Jun. 2, 2009) now U.S. patent application Ser. No. 12/792,365, filed Jun. 2, 2010. The details of the synthesis of these types of polymers are also described herein. A silyl ether-modified hydrophobic α(1→4)glucopyranose polymer is further described herein as a representative silane-containing hydrophobic biodegradable polymer which can be included in a polymer emulsion along with an arylboronic acid, such as a halogenated arylboronic acid.

Representative silyl ether-modified hydrophobic α(1→4) glucopyranose polymers include a first portion that is an α(1→4)glucopyranose polymeric backbone, a second portion that is a hydrophobic portion including hydrophobic groups that are pendent from the α(1→4)glucopyranose polymeric backbone, and a third portion that includes one or more silyl ether groups pendent from the poly-α(1→4)glucopyranose portion.

In a process similar to forming a hydrophobic polysaccharide as described herein, the silyl ether-modified hydrophobic α(1→4)glucopyranose polymer can be formed by reacting a compound having a hydrophobic group with a hydrocarbon segment, and a compound having a silyl ether group, with one or more portions of an α(1→4)glucopyranose polymer. This can provide silyl ether groups pendent from positions on the glucopyranose monomeric units previously corresponding to either or both primary and/or secondary hydroxyl locations. A hydrolytically-cleavable or hydrolytically-stable covalent bond between the silyl ether group and the glucopyranose unit of the polysaccharide backbone can be formed.

The silyl ether-modified hydrophobic α(1→4)glucopyranose polymer can include a monomeric unit according to formula III:

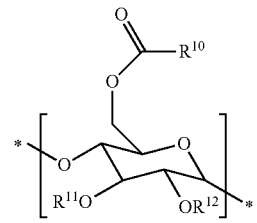

wherein $R^{10}$ is a $C_1$-$C_{18}$ hydrocarbon group, and more preferably $-(CH_2)_x CH_3$, wherein x is an integer in the range of 0-11; and
wherein $R^{11}$ and/or $R^{12}$ is:

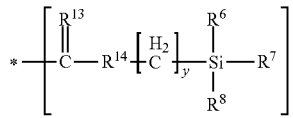

wherein $R^{13}$ is S or O, $R^{14}$ is C, O, N, or a covalent bond, y is an integer in the range of 2-8, $R^6$, $R^7$, and $R^8$ are independently selected from $R^9$ or $OR^9$, wherein $R^9$ includes a hydrocarbon group, such as a C1-C6-containing hydrocarbon group, or more specifically a linear or branched C1-C6 alkyl group, with the proviso that at least one of $R^6$, $R^7$, or $R^8$ is $OR^9$, and if one of $R^{11}$ or $R^{12}$ is not as defined above, then one of $R^{11}$ or $R^{12}$ is H.

In some aspects of formula III, $R^6$, $R^7$, and $R^8$, are all independently selected from $OR^9$, wherein $R^9$ is a C1-C6-containing hydrocarbon group, or more specifically, a linear or branched C1-C6 alkyl group. In some aspects of formula III, one of $R^6$, $R^7$, or $R^8$ is $OR^9$, wherein $R^9$ is a C1-C6-containing hydrocarbon group, or more specifically a linear or branched C1-C6 alkyl group, and the other groups that are not $OR^9$ are independently selected from $R^9$.

The functional silyl ether groups can be reacted to form a hydrophobic α(1→4)glucopyranose matrix, or to attach the hydrophobic α(1→4)glucopyranose polymer to a surface of a device.

Features of the silane-functionalized hydrophobic polysaccharide as described in U.S. Provisional Patent Application No. 61/217,625, such as number and/or density of the pendent hydrophobic and silane-containing groups on the α(1→4)glucopyranose polymer, the weight ratio between the hydrophobic and the poly-α(1→4)glucopyranose portion, are incorporated herein.

Poly(alkyl acrylate) or poly(aromatic acrylate) can be derivatized to add silane groups by a method such as described by Jin, X., et al. (1989) J. Mater. Sci., 24 3416-3420. In this method, silane-terminated polybutylmethacrylate (PBMAS) and polybutylacrylate are formed by free radical polymerization in toluene in the presence of 1% dimethyldichlorosilane which acts as a chain-transfer agent.

As described herein, a hydrolytically-cleavable group can be present between the hydrophobic group and the glucopyranose unit of the polysaccharide backbone. A silyl ether group can be used as the hydrolytic ally-cleavable group. In this aspect, the silyl ether group remains intact during matrix formation (i.e., unlike the silyl ether group of Formula II, it is not hydrolyzed to undergo covalent bonding to a target chemical group). Use of a silyl ether group in the linker segment can enhance degradation of the polymeric matrix formed from the emulsion composition of the invention after the matrix has been introduced in the body.

In some aspects, the hydrophobic α(1→4)glucopyranose polymer has a pendent group including silyl ether segment and one or more hydrophobic group(s) according to formula IV:

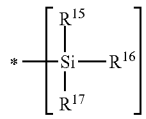

where one or more of $R^{15}$, $R^{16}$ and/or $R^{17}$ comprise a $C_1$-$C_{18}$ hydrocarbon group, with the proviso that the total number of carbon atoms in $R^{15}$, $R^{16}$, and/or $R^{17}$ is at least three.

The $C_1$-$C_{18}$ hydrocarbon group of one or more of $R^{15}$, $R^{16}$, and/or $R^{17}$ can be a linear, branched, or cyclic hydrocarbon structure. Combinations of linear, branched, or cyclic hydrocarbon structures can also be present in the pendent group. In some aspects, one or more of $R^{15}$, $R^{16}$, and/or $R^{17}$ is/are a linear $C_2$-$C_{18}$ hydrocarbon group. In some modes of practice, one or more of $R^1$, $R^2$, and/or $R^3$ is/are independently selected from methyl and ethyl. In some modes of practice, one of $R^{15}$, $R^{16}$, and/or $R^{17}$ is a $C_3$-$C_8$ hydrocarbon group. In some modes of practice, one of $R^{15}$, $R^{16}$, and/or $R^{17}$ is an iso-propyl or tert-butyl group.

A hydrophobic α(1→4)glucopyranose polymer with a silyl ether-containing linker segment between the hydrocarbon group and the glucopyranose backbone can be formed by reacting a compound that includes a hydrocarbon group and a reactive silicon group, with a hydroxyl group on the glucopyranose monomeric unit. The compound can include a hydroxyl-reactive, silyl ether-forming group. Compounds that can provide this type of linker chemistry when reacted with α(1→4)glucopyranose polymer include halogenated alkyl silanes and silazanes. Exemplary halogenated alkyl silanes include chlorotrimethyl-silane, chlorotriethylsilane, chlorodimethylethylsilane, and the like. In exemplary modes of practice, the reaction can be carried out in DMSO in the presence of a general base catalyst (e.g., imidazole), with the halogenated alkyl silane added in an amount to provide a desired level of polysaccharide derivation. In an exemplary mode of synthesis, maltodextrin is reacted with chlorotriethylsilane at a weight ratio of approximately 1:2, respectively (1 g:2 g).

The resulting hydrophobic α(1→4)glucopyranose polymer can include a derivatized monomeric unit of Formula V:

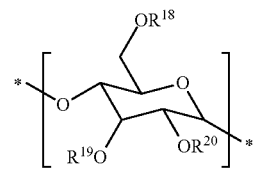

wherein one or more of $R^{18}$, $R^{19}$, and/or $R^{20}$ is according to IV:

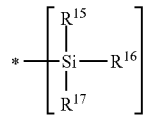

with $R^{15}$, $R^{16}$, and/or $R^{17}$ described herein.

An aliphatic polyester can be derivatized to add silane groups by a method such as described in Wang et al. (2001) Biomacromolecules, 2:1206-1213. As a general matter, silyl ether derivatization can be accomplished by the cross-dehydrocoupling polymerization of 1,3-bis(dimethylsilyl)benzene (BDSB) with a polyester (e.g., polycaprolactone (PCL)) diol macromonomer. The silane-coupled aliphatic polyester is prepared by mixing stoichiometric equivalents of PCL and BDSB, followed by addition of a solvent and a 0.25 mol % of 10 wt % Pd/C catalyst. After the cessation of hydrogen evolution, the temperature is raised to about 100° C. and maintained for 24 h. The polymer is then precipitated in cold methanol to yield a white solid, which was then dried in vacuo at room temperature.

Hydrophobic compounds, such as hydrophobic polymers, can be used in combination with an arylboronic acid, such as a halogenated arylboronic acid, to prepare emulsion compositions having exceptional stability. Exemplary polymeric emulsions of the invention are described in reference to those made with hydrophobic polysaccharides, hydrophobic polymers having pendent silane-containing groups, and specifically, silyl ether-modified hydrophobic α(1→4)glucopyranose polymers. Stable emulsions have been found to be particularly useful for the formation of polymeric matrices which can be prepared in various forms. For example, the polymeric matrices can be used as a medical material (e.g., a microparticulate, coating, etc.) for use in the body.

Arylboronic acids, such as halogenated arylboronic acids, are useful for the stabilization of various emulsion types, including simple emulsions such as oil-in-water-types of emulsions (O/W emulsions), as well as water-in-oil-types of emulsions (O/W emulsions). The arylboronic acids are also useful for the stabilization of more complex (W/O/W) multiple emulsions.

Emulsions are characterized by a continuous phase and a discontinuous phase, with the continuous phase (generally in liquid form) surrounding colloid structures (e.g., polymeric microparticles) of the discontinuous phase. In O/W emulsions the distribution of a hydrophobic compound, such as a hydrophobic polymer, is in the dispersed phase. Depending on the properties of the hydrophobic compound (for example, whether it is a liquid or a solid), the compound can be dispersed by itself as discontinuous phase particulates, or can be dissolved in a solvent (e.g. an organic solvent), which then forms the discontinuous phase structures in the emulsion.

Microparticles can be formed from O/W emulsions containing a hydrophobic polymer and an arylboronic acid, such as a halogenated arylboronic acid. In some cases, a reactive chemistry associated with hydrophobic polymer (such as a silyl-ether chemistry) can be used to cause crosslinking in the microparticle.

An arylboronic acid, such as a halogenated arylboronic acid, can be dissolved or suspended in a phase of the emulsion. Whether the arylboronic acid is present continuous or discontinuous phase depends on the type(s) of liquids used to prepare the emulsion, and the arylboronic acid used.

In some aspects, the arylboronic acid, such as a halogenated aryl boronic acid, is dissolved in a discontinuous phase. The aryl boronic acid can be dissolved in a solvent, or combination of solvents, used to dissolve the hydrophobic polymer of the emulsion. In one mode of practice the aryl boronic acid and the hydrophobic polymer(s) are dissolved in a solvent that includes methanol, dichloromethane, chloroform, ethyl acetate, or a hexane. In some cases one or more other co-solvents are included along with methanol. The cosolvent can be used for dissolution of the hydrophobic polymer, and is miscible with the methanol.

Alternatively, the arylboronic acid, such as a halogenated aryl boronic acid, is suspended in a continuous phase liquid in the emulsion. In these aspects, the aryl boronic acid may have limited or no solubility in the continuous phase liquids that are used to form the emulsion.

An oil-in-water-type of emulsion can be prepared by dissolving the hydrophobic polymer in a discontinuous phase liquid (organic) including a solvent such as dichloromethane, chloroform, or a similar solvent that is immiscible with water. Optionally, the discontinuous phase liquid can be mixed with a secondary solvent, such as an alcohol like methanol.

Amounts of hydrophobic polymer dissolved in the discontinuous phase liquid can depend on one or more factors, such as the solubility of the polymer in the liquid, or the desired amount of polymer to form particulate structures. In some modes of practice, an amount of hydrophobic polymer in the range of about 0.05 mg/mL (~0.005% wt) to about 50 mg/mL (~5% wt), and more specifically in the range of about 0.2 mg/mL (~0.02% wt) to about 20 mg/mL (~2% wt) is present in the discontinuous phase liquid.

As discussed herein, an arylboronic acid, such as a halogenated arylboronic acid, is dissolved in the discontinuous phase or suspended in the continuous phase, or both.

In some aspects, the arylboronic acid (such as dichlorophenylboronic acid (DPBA)) is dissolved in the discontinuous phase liquid along with the hydrophobic polymer. To facilitate dissolution of the arylboronic acid, the discontinuous phase liquid (organic) can include an alcohol such as methanol. In one mode of practice, the discontinuous phase liquid (organic) includes a hydrophobic polymer and arylboronic acid, a first solvent selected from dichloromethane and chloroform, and a second solvent selected from an alcohol such as methanol. In some aspects, the first and second solvents are present in the discontinuous phase liquid at volume to volume ratio in the range of 20:1 to 2:1, respectively. One exemplary discontinuous phase solvent system is a binary mixture of dichloromethane and methanol at a 9:1 (v/v) ratio.

In some aspects, an arylboronic acid, such as a halogenated arylboronic acid, is present discontinuous phase liquid (organic) at a concentration in the range of about 0.05 mg/mL (~0.005% wt) to about 50 mg/mL (~5% wt), and more specifically in the range of about 0.2 mg/mL (~0.02% wt) to about 20 mg/mL (~2% wt).

Alternatively, an arylboronic acid, such as a halogenated arylboronic acid, is present in the continuous phase. The arylboronic acid may have limited or no solubility in the liquid of the continuous phase and therefore can be present in the form of suspended or dispersed particles. Such suspensions can be prepared by adding the arylboronic acid to the continuous phase liquid and then treating the mixture using a blender or a sonicator to suspend the arylboronic acid in the liquid.

The arylboronic acid, such as a halogenated arylboronic acid, can be suspended in the continuous phase liquid in amounts similar to the amounts used for dissolution in the discontinuous phase (i.e., about 0.05 mg/mL (~0.005% wt) to about 50 mg/mL (~5% wt), and more specifically in the range of about 0.2 mg/mL (~0.02% wt) to about 0.2 mg/mL (~2% wt).

If the arylboronic acid, such as a halogenated arylboronic acid, is suspended in the continuous phase, depending on the type of discontinuous phase liquid that is used to prepare the emulsion, at least a portion of the arylboronic acid may become dissolved in the discontinuous phase. If this is the case, during emulsion formation the concentration of the arylboronic acid can decrease in the continuous phase.

The discontinuous phase liquid with the hydrophobic polymer can also include one or more bioactive agents. If a bioactive agent is present, it can be soluble in the solvent or solvent system that is used to dissolve the hydrophobic polymer.

Next, the oil phase polymer solution can be combined with water (with the arylboronic acid present in either the oil/polymer mixture or the discontinuous aqueous phase). The oil/polymer mixture can be added to an excess amount of water (or suitable aqueous phase liquid). A suitable excess volume can be about 10 times the volume of the polymer solution or greater. The mixture is then emulsified using a high-speed blender, mixer, homogenizer, or other equipment that promotes emulsion formation. The addition of water and emulsion blending promotes the formation of microparticles containing the hydrophobic polymer. If a bioactive agent is present in the discontinuous phase, it can become entrapped in the polymer matrix that forms the microparticles.

The formed microparticles can then be further processed from the emulsion. Such processing can involve the isolation of the microparticles using conventional techniques, such as centrifugation and washing. Solvent extraction and/or evaporation can be used to remove organic solvent from the microparticles. If washes are carried out and arylboronic acid is present in the microparticles, it can be washed away using a washing solution that includes methanol, or similar solvent.

If the hydrophobic polymer includes reactive groups (such as moisture-sensitive reactive silyl ether-containing groups) a step in the emulsion process can promote reaction and polymer-polymer crosslinking.

An arylboronic acid, such as a halogenated arylboronic acid, can also be useful for the stabilization of multiple emulsions, such as water-in-oil-in-water (W/O/W) multiple emulsions. W/O/W multiple emulsions are emulsion systems where small aqueous droplets are entrapped within larger oil-phase droplets that in turn are dispersed in a continuous aqueous phase. W/O/W multiple emulsions can be used to prepare colloidal systems wherein a bioactive agent is present small droplets, which in turn are surrounded (encapsulated) by the oil phase, which includes a hydrophobic compound, such as a hydrophobic polymer. The particles in the emulsion can be further processed so the hydrophobic compound forms a hydrophobic bather layer around the bioactive agent-containing droplets, thereby forming a microparticulate with a core-shell type of structure.

The emulsions of the invention can be used to prepare microparticles wherein the hydrophobic polymeric barrier is used to modulate release of the bioactive agent from the formed particulate. In some cases, a reactive chemistry associated with hydrophobic polymer (such as a silyl-ether chemistry) can be used to cause crosslinking of the polymeric material forming the barrier layer.

To prepare a W/O/W multiple emulsion, first, a small amount of a discontinuous aqueous phase solution is prepared. This aqueous phase solution may include a bioactive agent that is soluble in the aqueous liquid, such as a large molecule bioactive agent that is based on a polypeptide, polysaccharide, or polynucleotide. The bioactive agent can be present at a high concentration (e.g., in a saturated solution) to maximize the amount of bioactive agent to be encapsulated by the polymeric material.

The aqueous phase solution can then be added to an oil phase solution (continuous) that includes a hydrophobic polymer and an arylboronic acid, such as a halogenated arylboronic acid. Again, an exemplary amount of hydrophobic polymer can fall in the range of 0.05 mg/mL (0.005% wt) to about 50 mg/mL (5% wt), and an exemplary amount of arylboronic acid can be in the range of about 0.05 mg/mL (0.005% wt) to about 50 mg/mL (5% wt).

The amount of an arylboronic acid, such as a halogenated arylboronic acid, present in the organic phase can also be described in relation to the amount of hydrophobic compounds present. For example, in some aspects the arylboronic acid and hydrophobic compound (e.g., hydrophobic polymer) are present in the organic phase at a weight ratio in the range of about 1:10 to about 1:5000, or more specifically, in the range of about 1:30 to about 1:100, respectively.

The aqueous phase solution can be added as a fraction of the overall amount of polymer solution (such as in the range of about 1:500 to about 1:10 v/v water:polymer solution). The mixture is then emulsified using a high speed blender. The addition of water and emulsion blending promotes the formation of microdroplets of water, which are surrounded by the hydrophobic polymer, and the emulsion is stabilized by the arylboronic acid. In the case where the hydrophobic polymer includes a moisture sensitive reactive group (such as a silyl ether group) the formation of a crosslinked polymer shell around the microdroplets can be promoted.

Next, this water-in-oil emulsion is taken and dispersed in an aqueous solution. A suitable excess volume can be about 10 times the volume of the polymer solution or greater. This secondary mixture can also be emulsified using a high speed blender. In this process the original continuous oil phase polymer and arylboronic acid becomes the discontinuous phase, and the microdroplets with polymeric shells are formed. In the case where the polymer includes a moisture sensitive reactive group (such as a silyl ether group) further polymer crosslinking of the polymer in the shell can occur.

An exemplary emulsion includes a hydrophobic polymer comprising a reactive silane group (e.g., silane ether) and an arylboronic acid, such as a halogenated arylboronic acid. The hydrophobic polymer can be present in the oil phase of the emulsion and subsequently reacted to promote formation of a hydrophobic polymeric matrix. The polymeric matrix can be in the form of a solid polymeric microparticles (e.g., with bioactive agent), or as a polymeric shell which encapsulates a bioactive agent-containing core. For example, pendent silyl ether groups on a hydrophobic polymer are reacted to crosslink the polymers in the oil phase via a siloxane linkage. The siloxane linkage can be formed through a condensation reaction.

In some instances, crosslinking can occur by hydrolysis of a silyl ether group, and subsequent reaction with a silane group through a condensation reaction. Silane-containing groups can associate by hydrogen bonding, and then an increase in temperature can promote the condensation reaction. Crosslinking can also occur through formation of silanol group following loss of the alkyl radical, and subsequent reaction with a silane group accompanies loss of a water molecule. The extent of crosslinking can be modulated by the reaction conditions including time, heat, etc. The bonding reaction can be carried out in aqueous conditions (for example, with the formation and hydrolysis of silanol groups), or in non-aqueous conditions.

Silanol formation and crosslinking of a polymer having a reactive silane group can be promoted by adjusting the pH of a composition that includes the hydrophobic polymer comprising a reactive silane group. For example, in some modes of practice, silanol formation and crosslinking is promoted under either basic or acidic conditions. The pH can be adjusted using suitable inorganic or organic acids and bases, and stabilized. Exemplary bases and acids include carbonate and hydroxide salts, hydrochloric and citric acid, respectively.

Generally, microparticles formed in the stabilized emulsions have a size in the range of about 5 nm to about 100 μm in diameter, about 50 nm to about 50 μm in diameter, or about 250 nm to about 10 μm in diameter. The microparticles can be spherical or somewhat spherical in shape.

As discussed, the emulsion can also include one or more bioactive agents. The bioactive agents can become associated (e.g., entrapped) in the hydrophobic polymeric particulates formed during the emulsion process. Depending on factors such as the property of the bioactive agent, and the method for preparing the emulsion, the bioactive agent can be associated with the particulate in a certain manner. For example, for a bioactive agent that is mixable or blendable with a hydrophobic polymer, the bioactive agents may be dispersed throughout the particulate which can be formed using an O/W emulsion method described herein.

For bioactive agents that are not mixable or blendable with a hydrophobic polymer, the bioactive agents can be located in a discrete portion of the particulate (for the bioactive agents can be present in the core of a particulate and surrounded by a hydrophobic polymeric shell). These particulates can be formed using an W/O/W emulsion method described herein.

In one mode of practice, the emulsion comprises a bioactive agent that is blendable with a hydrophobic polymer. The blendability can be determined by the ability of a particular solvent (e.g., an organic solvent such as dichloromethane) to dissolve both the bioactive agent and the hydrophobic polymer. Particulates can be formed that include the bioactive agent and hydrophobic polymer.

For preparation of an emulsion, a composition can be prepared that includes the bioactive agent and the hydrophobic polymer dissolved in a solvent or a solvent system (e.g., combination of solvents). The amounts of solvent and bioactive agent can be chosen based on one or more factors such as the desired loading of the bioactive agent in the particulate, the amount of hydrophobic polymer needed to form the particulate, and the desired control of bioactive agent release.

The term "bioactive agent," refers to an inorganic or organic molecule, which can be synthetic or natural, and that causes a biological effect when administered in vivo to an animal, including but not limited to birds and mammals, including humans. The bioactive agent can be present in the emulsion composition, or in an injectable or implantable composition formed from the composition in an amount suitable to affect a condition to be treated with the bioactive agent.

A partial list of bioactive agents is provided below. One may choose one or more of the bioactive agents to be included or associated with a matrix formed from a hydrophobic polymer. A comprehensive listing of bioactive agents, in addition to information of the water solubility of the bioactive agents, can be found in The Merck Index, Thirteenth Edition, Merck & Co. (2001).

Polymeric matrices, such as in the form of microparticles, and coatings prepared according to the invention can be used to release bioactive agents falling within one or more of the following bioactive agent classes. These classes include, but are not limited to: ACE inhibitors, actin inhibitors, analgesics, anesthetics, anti-hypertensives, anti polymerases, antisecretory agents, anti-AIDS substances, antibiotics, anti-cancer substances, anti-cholinergics, anti-coagulants, anti-convulsants, anti-depressants, anti-emetics, antifungals, anti-glaucoma solutes, antihistamines, antihypertensive agents, anti-inflammatory agents (such as NSAIDs), anti metabolites, antimitotics, antioxidizing agents, anti-parasite and/or anti-Parkinson substances, antiproliferatives (including antiangiogenesis agents), anti-protozoal solutes, anti-psychotic substances, anti-pyretics, antiseptics, anti-spasmodics, antiviral agents, calcium channel blockers, cell response modifiers, chelators, chemotherapeutic agents, dopamine agonists, extracellular matrix components, fibrinolytic agents, free radical scavengers, growth hormone antagonists, hypnotics, immunosuppressive agents, immunotoxins, inhibitors of surface glycoprotein receptors, microtubule inhibitors, miotics, muscle contractants, muscle relaxants, neurotoxins, neurotransmitters, polynucleotides and derivatives thereof, opioids, photodynamic therapy agents, prostaglandins, remodeling inhibitors, statins, steroids, thrombolytic agents, tranquilizers, vasodilators, and vasospasm inhibitors.

The emulsion can optionally include additional hydrophobic components (secondary, etc.) that are different than the primary hydrophobic component (e.g., hydrophobic polymer). For example, these additional components can be, but are not limited to, other hydrophobic polymers, fats, and oils. For example, the emulsion can include a blend of two different hydrophobic polymers. These optional hydrophobic components can be bendable with the primary hydrophobic component. In combination with the primary hydrophobic component, the optional hydrophobic components may enhance the formation, structure, and/or stability of microparticulates, or other articles that can be implanted or injected into the body.

Optionally, the emulsion can include secondary stabilizers that promote formation of the microparticles. Exemplary secondary stabilizers include water soluble components such as poly(vinyl alcohol). Poly(vinyl alcohol)s that have been used as emulsion stabilizers include those having a molecular weight in the range of about 10 kDa to 30 kDa. Another exemplary secondary stabilizer is PLURONIC™ F68 (an ethylene oxide/propylene oxide block copolymer). Water soluble secondary stabilizers can be included in the aqueous phase of an O/W or W/O/W emulsion if desired. Stabilizers such as poly(vinyl alcohol) are typically used at concentrations in the range of about 0.1% wt to about 5% wt (about 1 mg/mL to about 50 mg/mL).

Optionally, the emulsion can include one or more surfactants. The surfactants can promote formation of provide further stability to the emulsion, or promote the formation of particular discontinuous phase structures. Nonionic and ionic (including cationic and anionic) surfactants can optionally be used in the emulsion. If a surfactant is used it can be chosen based on its hydrophilic-lipophilic balance, which is the measure of the water or oil solubility of the surfactant. Exemplary amounts for surfactants in the emulsion are about 5 wt % or less, such as in the range of about 0.1 wt % to about 5 wt %.

Additional excipients can be added to the emulsion as desired. If the emulsion or microparticles formed therefrom are intended for internal use, an additional excipient component can be pharmaceutically acceptable. Additional excipients can include additives or auxiliary substances such as an antioxidants, antiseptics, isotonic agents, and buffering agents. These excipients can be used to stabilize a bioactive agent or the microparticle in which the bioactive agent is included.

With the addition of an arylboronic acid emulsion stabilizer, such as a halogenated arylboronic acid, hydrophobic polymer-containing emulsions have been found in stable form (i.e., the emulsion droplets do not show obvious destabilization, such as coalesce to form two distinct continuous phases) for periods greater than about 24 hours, or greater than about 170 hours, such as up to about 670 hours. The stability of the emulsions is measured at a temperature of about 23° C. Therefore, a "stabilized" emulsion refers to those demonstrating stability of at least 24 hours.

After the emulsion has formed it can be further processed using one or more processing steps. In some aspects, the microparticles present in the emulsion can be isolated, for example, separated from the continuous phase liquid that they are dispersed within. Common techniques for separation include centrifugation and filtration.

After the microparticles have been isolated by centrifugation, the continuous phase liquid can be removed by decanting or aspiration. If desired, the microparticles can be washed using a non-solvent for the microparticles (i.e., a liquid that does not dissolve the microparticles). In this step, a washing liquid can be used that removes remaining arylboronic acid from the microparticle preparation. For example, the wash liquid can include methanol.

A washing liquid can also remove any discontinuous phase solvent from the microparticles. Removal of any discontinuous phase solvent can be achieved by using a wash liquid in which the discontinuous phase solvent is soluble, but that does not cause dissolution of the polymeric microparticles. Alternatively, any discontinuous phase solvent can be removed by placing the isolated microparticles under a low-pressure environment. The microparticle preparation can also be lyophilized using standard equipment and techniques.

Microparticles that are formed from an arylboronic acid emulsion, such as a halogenated arylboronic acid emulsion, can also be processed into other forms to provide an implantable or injectable article is a desired configuration or shape. Given this, the current invention also contemplates microparticle formation as a general way to form a hydrophobic polymeric article of other types and configurations. In general, after the emulsion has been formed, it can be used to create a polymeric matrix in a certain form (herein referred to as an "article" that includes the polymeric matrix formed from the hydrophobic polymer).

The various oil-in-water-types of emulsions, or the water-in-oil-types of emulsions described herein can be used to form microparticles having crosslinked polymers, which are subsequently processed to a second desired form. For example, when a reactive silane-containing hydrophobic polymer is used, the method can involve a step of removing all or a portion of water from the polymer-containing compositions (e.g., a drying step) which promotes formation of siloxane bonds between the hydrophobic polymers, or to a secondary material, such as a device surface.

The emulsion can be used to form articles that are wholly degradable, partially degradable, or biostable. A partially degradable article can be an article that has a biostable portion, such as a biostable body member, and a biodegradable portion, such as a biodegradable coating.

The polymeric matrices formed from the inventive emulsions can be used in many medical applications. These include drug delivery medical applications, as well as applications where drug delivery is not required. The applications can involve short term or long-term treatment of various conditions.

In some aspects, microparticles from the emulsion are further processed to form an implantable or injectable medical article which also includes a bioactive agent. The implant may not have any distinct mechanical properties, such as would be apparent with an intravascular prosthesis, but rather provides a mechanism to deliver the bioactive agent to a particular portion of the body. The implant can have a defined structure and size that is appropriate for its use at a desired location in the body. A medical implant having a defined structure can be formed by any suitable process, including molding, extruding, shaping, cutting, casting, and the like.

The implantable or injectable medical article can include a matrix formed of the hydrophobic polymer which modulates the release of the bioactive agent from the article. In some cases, the matrix is in the form of a barrier layer that the bioactive agent passes through before becoming available to the subject. Such a barrier layer can be in the form of a shell of polymeric material encapsulating a core comprising bioactive agent.

In some aspects, the emulsion can be used to form a body member, or a portion of a body member, of an implantable medical article. In these aspects, a degradable body member, or portion thereof, can provide mechanical properties at the implantation site and can maintain these mechanical properties until they are no longer needed. After a period of time has elapsed, the body member is degraded to an extent that the mechanical properties are no longer provided, and the degraded components of the article are processed by the body.

In some embodiments, the body member of the medical article slowly degrades and transfers stress at the appropriate rate to surrounding tissues as these tissues heal and can accommodate the stress once borne by the body member of the medical article. The medical article can optionally include a coating or a bioactive agent to provide one or more additional functional features, however, these are not required in order for the article to be of use at the treatment site.

The article can also comprise filaments and fibers, such as microfibers and/or nanofibers that are formed from an emulsion including a hydrophobic polymer. The filaments or fibers can be included in or associated with various articles including implantable medical articles. The filaments or fibers may be prepared with a bioactive agent to provide one or more additional functional features.

In some modes of practice, the emulsion composition can be used to provide a coating or film. Although the emulsion composition can be used to form a coating or film on any desired surface, the method is exemplified for forming a coating on the surface of a medical device. The emulsion composition can be applied to a medical device using standard techniques to cover the entire surface of the device, or a portion of the device surface. If more than one coated layer is applied to a surface, it is typically applied successively. For example, a coated layer can be formed by, for example, dipping, spraying, bushing, or swabbing the emulsion composition on the surface of the device.

An exemplary spray coating process and apparatus that can be used for coating implantable medical articles using the compositions of the present invention is described in U.S. Pat. No. 7,192,484 (Chappa et al.)

A "coating" as used herein can include one or more "coated layers", each coated layer including one or more coating materials. In some cases, the coating can be formed of a single layer of material that includes a hydrophobic polymer. In other cases, the coating includes more than one coated layer, at least one of the coated layers includes a hydrophobic polymer. If more than one layer is present in the coating, the layers can be composed of the same or different materials.

In some aspects, the hydrophobic polymer includes a silyl ether group that is reacted with a material on the surface of article (such as a medical device) to form a coated layer, wherein the hydrophobic polymer becomes bonded to the material surface via a siloxy group.

The following list of medical articles is provided to illustrate various medical articles that can that can be associated with a polymeric matrix made using the emulsion compositions of the invention. These types of articles are typically introduced temporarily or permanently into a mammal for the prophylaxis or treatment of a medical condition. For example, these articles can be introduced subcutaneously, percutaneously or surgically to rest within an organ, tissue, or lumen of an organ, such as arteries, veins, ventricles, or atria of the heart.

Exemplary medical articles include vascular implants and grafts, grafts, surgical devices; synthetic prostheses; vascular prosthesis including endoprosthesis, stent-graft, and endovascular-stent combinations; small diameter grafts, abdominal aortic aneurysm grafts; wound dressings and wound management device; hemostatic barriers; mesh and hernia plugs; patches, including uterine bleeding patches, atrial septic defect (ASD) patches, patent foramen ovale (PFO) patches, ventricular septal defect (VSD) patches, and other generic cardiac patches; ASD, PFO, and VSD closures; percutaneous closure devices, mitral valve repair devices; left atrial appendage filters; valve annuloplasty devices, catheters; central venous access catheters, vascular access catheters, abscess drainage catheters, drug infusion catheters, parenteral feeding catheters, intravenous catheters (e.g., treated with antithrombotic agents), stroke therapy catheters, blood pressure and stent graft catheters; anastomosis devices and anastomotic closures; aneurysm exclusion devices; biosensors; cardiac sensors; birth control devices; breast implants; infection control devices; membranes; tissue scaffolds; tissue-related materials; shunts including cerebral spinal fluid (CSF) shunts, glaucoma drain shunts; dental devices and dental implants; ear devices such as ear drainage tubes, tympanostomy vent tubes; ophthalmic devices; cuffs and cuff portions of devices including drainage tube cuffs, implanted drug infusion tube cuffs, catheter cuff, sewing cuff; spinal and neurological devices; nerve regeneration conduits; neurological catheters; neuropatches; orthopedic devices such as orthopedic joint implants, bone repair/augmentation devices, cartilage repair devices; urological devices and urethral devices such as urological implants, bladder devices, renal devices and hemodialysis devices, colostomy bag attachment devices; biliary drainage products.

Implantable or injectable medical articles associated with a matrix formed from an emulsion containing a hydrophobic polymer can be sterilized. Sterilization can take place prior to using the medical article and/or, in some cases, during implantation of the medical article.

Articles formed from the emulsions of the invention can be used in a subject for the treatment of a medical condition. Bioactive agents incorporated into articles formed from the emulsions of the invention can release a desired amount of the agent over a period of time. For example, bioactive agent can be released from a biodegradable microparticle upon its degradation in vivo.

In performing the method, the article is placed in a subject. If a biodegradable matrix is used, upon exposure to body fluid the bioactive agent is released from a portion of the article. In some cases, depending on the type of degradable hydrophobic polymer used, the matrix is subjected to degradation by non-enzymatic hydrolysis, enzymatic amylase activity, or both.

The invention will be further described with reference to the following non-limiting Examples.

EXAMPLE 1

Preparation of Fractionated Maltodextrin

Maltodextrin was purchased from Roquette, France (GLUCIDEX™ 2, $MW_{ave}$ 320 kDa) or Grain Processing Corporation, Muscatine, Iowa (M040 $MW_{ave}$ 55 kDa). The 55 kDa maltodextrin was used as received. GLUCIDEX™ 2 was further fractionated to a narrower polydispersity.

GLUCIDEX™ 2 maltodextrin (MD; 500 g; DE=3 max) was dissolved in deionized water to a total volume of 5 L with stirring, and diafiltered using a 500 kDa molecular weight cut-off cassette, and the permeate (flow through) was kept. The permeate was then diafiltered using a 100 kDa weight cut-off cassette and the retenate was kept. The solution was concentrated down to 3 L and then lyophilized. 310 g of maltodextrin (100-500 kDa) was isolated (62% yield).

EXAMPLE 2

Preparation of Hydrophobic Maltodextrin, "MD-Hex"

Reagents were purchased from Aldrich and were used as received unless noted. Solvents were not pre-dried prior to reaction unless noted. Maltodextrin (20 g) from either the 55 kDa preparation or the 100-500 kDa preparation as described in Example 1 was taken up in anhydrous DMSO (200 mL). 1-methylimidazole (21 mL, 0.263 mol), was added to the maltodextrin solution, and stirred for 5 min. Hexanoic anhydride (50 mL, 0.217 mol) was then added to the reaction mixture, and stirring was continued for an additional 2 hr at room temperature. The reaction was quenched by pouring the reaction mixture into water (500 mL) at room temperature. The mixture was then blended in Waring blender for less then one minute. The product (maltodextrin-hex) formed a white solid which was collected by vacuum filtration and washed with water (10×100 mL). 21.7 g of product was obtained. To further purify maltodextrin-hex, it was dissolved in acetone and placed into 1,000 MWCO dialysis tubing and dialyzed against acetone (3×1 L) for 3 days at room temperature. Solution from dialysis tube was collected and solvent was removed in vacua. The resulting white solid was dried in vacuo. The maltodextrin-hex products had a degree of substitution with hexanoate groups (DS-hex) of 1.5, and molecular weights (ave) of starting maltodextrin 55 kDa and 320 kDa.

Similar procedures were performed, with variation in the amount of hexanoic anhydride used. These procedures provided maltodextrin-hex products with degrees of substitution of hexanoate groups (DS-hex) of 0.9 and 2.1, and molecular weights (ave) of starting maltodextrin 120 kDa and 320 kDa, respectively.

EXAMPLE 3

Preparation of Siloxy Ether Derivatized Hydrophobic Maltodextrin, "MD-Hex Silane"

MD-Hex (DS-hex=0.9, 2.0 g), as described in Example 2, was placed into 50 mL oven-dried flask under inert atmosphere and dissolved in anhydrous $CH_2Cl_2$ (20 mL) at room temperature. DMAP (0.1 g, 0.819 mmol; 4-dimethylaminopyridine) was added to the MD-Hex solution and reaction mixture was allowed to stir for an additional 5 min. After this, 3-isocyanatopropyltriethoxysilane (4.0 mL, 16.2 mmol) was added via syringe over 30 sec. The mixture was allowed to stir for an additional 70 hr at room temperature under inert atmosphere. Reaction mixture was then filtered and the solvent evaporated in vacuo. The crude product, including the silylether modified MD-hex (MD-Hex-silane), was dissolved in acetone and placed into 12,000-14,000 MWCO dialysis tubing and dialyzed against acetone (3×1 L) for 3 days. Solution from dialysis tube was collected and the solvent was removed in vacuo. The resulting white solid was dried in vacuo, with the process providing 1.5 g of solid.

The levels of derivations of the MD-hex silane products are listed in Table 1.

EXAMPLE 4

Preparation of Siloxy Ether Derivatized Hydrophobic Maltodextrin, MD-Hex Silane

MD-Hex (DS=2.1, 3.0 g), as described in Example 2, was placed into a 50 mL oven-dried flask under inert atmosphere and dissolved in anhydrous $CHCl_3$ (25 mL) at room temperature. Next, 3-isocyanatopropyltriethoxysilane (0.1 mL, 0.404 mmol) was added via syringe to the MD-Hex solution and the reaction mixture was allowed to stir for additional 16 hr at room temperature under an inert atmosphere. The reaction mixture was then filtered, diluted with $CHCl_3$ to 150 mL and kept at 4° C. for further use.

The levels of derivations of the MD-hex silane products are listed in Table 1.

TABLE 1

| Polymer | MW maltodextrin | DS Hex | Theor DS Silane |
|---------|-----------------|--------|-----------------|
| A | 320 kDa | 1.5 | 1.2 |
| B | 55 kDa | 1.5 | 0.6 |
| C | 120 kDa | 0.9 | 2.1 |
| D | 320 kDa | 2.1 | 0.05 |
| E | 55 kDa | 1.5 | 0.04 |

EXAMPLE 5

Emulsion Formation Using Siloxy Ether Derivatized Hydrophobic Maltodextrin and Various Additives The preparation of emulsion formulations were attempted for mixtures of MD-hex-silane solutions with aqueous solutions having various additives.

A MD-Hex-silane solution was prepared by dissolving MD-Hex-silane (polymer D in Table 1: 56 kDa, DS hex 1.5, DS silane 0.04 (theor.)) in dichloromethane at 10 mg/mL. The following aqueous solutions or suspensions were made using DDW as shown in Table 2.

TABLE 2

| Solution | Component | Amount | Notes |
|---|---|---|---|
| A | (water only) | | |
| B | Sodium borate (borax) | 10 mg/mL | |
| C | Boric acid | 10 mg/mL | |
| D | Phenylboronic acid | 10 mg/mL | Dissolved using sonic bath |
| E | 3,5-dichlorophenylboronic acid | 10 mg/mL | Did not dissolve, used as suspension |
| F | acetic acid | 1% | |
| G | N-cyclohexyl-3 aminopropanesulfonic acid (CAPS) buffer (pH ~9) | 10 mM | |

Figure 1B:
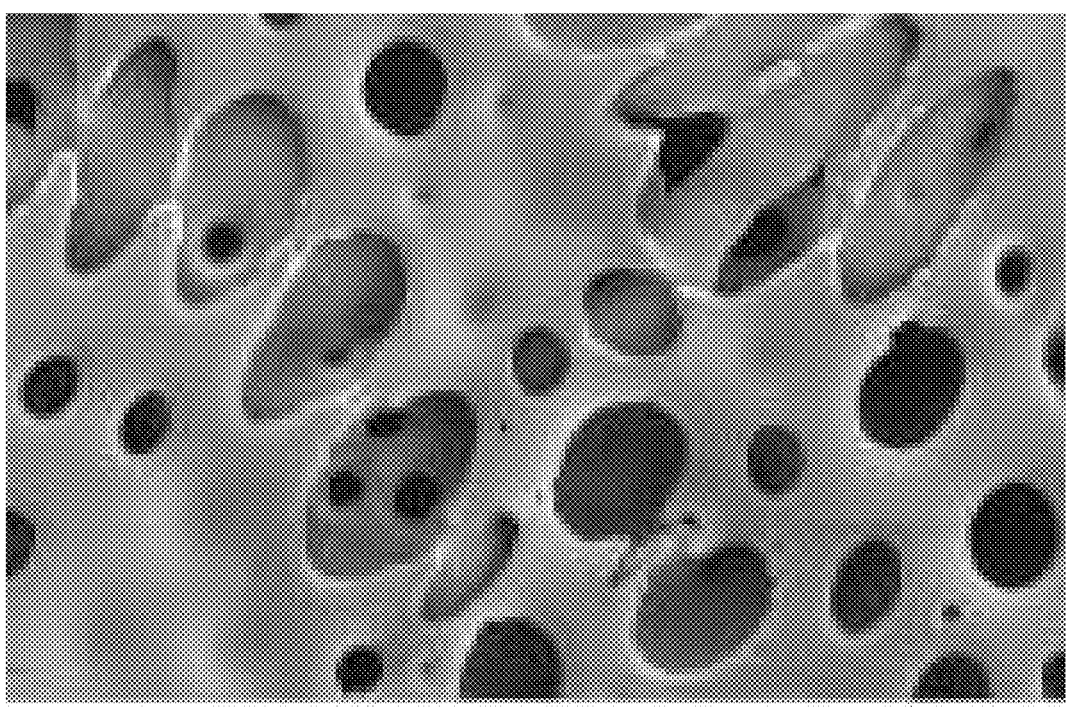
Figure 1C:
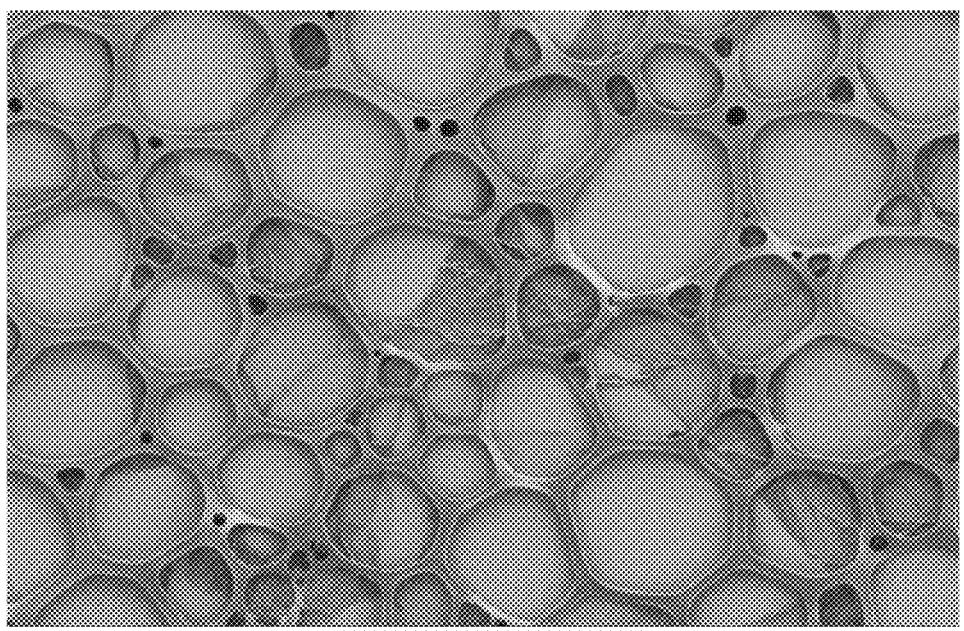

In plastic vials, 5 mL of the MD-Hex-silane solution in dichloromethane was pipetted. 100 μL of each of the aqueous solutions A-G were individually added to the MD-hex-silane solutions and the mixtures were homogenized at 12.4 kRPM for 2 min using a AKI25T homogenizer. Next, a small stir-bar was added to each mixture, which were then stirred for 4 hours at room temperature. The initially suspended dichlorophenylboronic acid immediately dissolved in the MD-Hex-silane solution and similar emulsions were obtained. After 4 hours, 5 μL was taken of each sample, placed on a glass slide, and then air-dried. SEM and light microscope pictures were taken. FIGS. 1A-1C show micrographs of air-dried emulsions of silyl ether-modified hydrophobic α(1→4)glucopyranose polymer. All emulsions were stable for several hours. Typically the emulsion in chloroform creams, however, upon light shaking the emulsion is restored. Overnight, however, some emulsions started to separate, forming bigger water droplets and continuous phases. In samples with boric acid, acetic acid and caps buffer very little remained emulsified. Water, borax and phenylboronic acid still had significant amount of dispersed emulsion, but a drop of continuous aqueous phase of about 5 mm was noticed. The sample containing dichlorophenylboronic acid (DPBA) was still completely emulsified. Results are discussed in Table 3.

TABLE 3

| Emulsion (MD-Hex-silane solution)+ | Notes |
|---|---|
| A[2] | Significant amount of dispersed emulsion at 24 hours, but a drop of continuous aqueous phase of about 5 mm noticed |
| B[2] | Significant amount of dispersed emulsion at 24 hours, but a drop of continuous aqueous phase of about 5 mm noticed |
| C[1] | Emulsion was substantially separated after 24 hours |
| D[2] | Significant amount of dispersed emulsion at 24 hours, but a drop of continuous aqueous phase of about 5 mm noticed |
| E[3] | Completely emulsified at 670 hours |
| F[1] | Emulsion was substantially separated after 24 hours |
| G[1] | Emulsion was substantially separated after 24 hours |

[1]least stable
[2]moderately stable
[3]most stable

EXAMPLE 6

Microparticle Formation Using Siloxy Ether Derivatized Hydrophobic Maltodextrin and Various Additives A solution of 1 mg/mL MD-Hex-silane (polymer D in Table 1: 56 kDa, DS hex 1.5, DS silane 0.04 (theor.)) was made in dichloromethane. Dichlorophenylboronic acid (DPBA) in an amount of 10 mg was dissolved in 1 mL in a mixture of dichloromethane/methanol (9:1 ratio). 5 mL aliquots of the MD-Hex-silane solution were pipetted into glass vials and 5 μL of the DPBA solution was added. In a separate vial, 5 μL of the DPBA solution was added to 5 mL of DCM without any polymer. Increasing amounts of water was pipetted (10 μL-500 μL) into the MD-Hex-silane/DPBA mixtures and dispersed (24 kRPM, 2 min) using AKI 25T homogenizer. The DCM (only) sample immediately separated after emulsification. All other dispersions were observed to cream, but were stable for several weeks leaving them at room temperature.

The emulsified MD-Hex-silane/DPBA mixture was then dried on a glass plate under vacuum for several hours. Chloroform added to the dried samples was able to completely dissolve the material, indicating that if any silanol crosslinking of the had occurred, the crosslinking was reversible.

Figure 2:
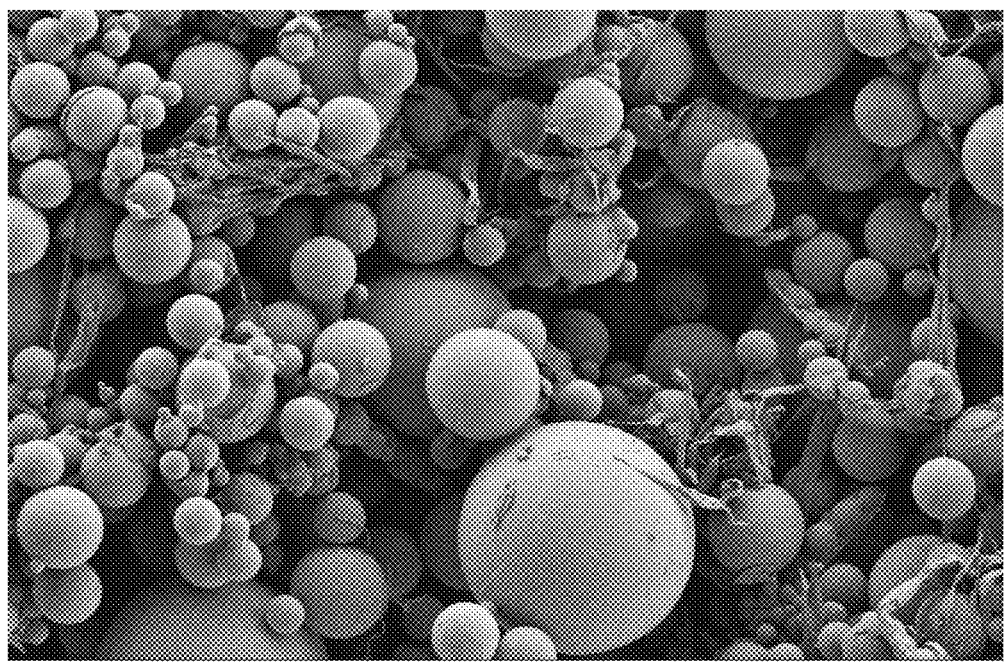
FIG. 2 is a micrograph of microparticles formed using the silyl ether-modified hydrophobic α(1→4)glucopyranose polymer.

Similar to Example 5, an emulsion was formed by addition of 100 μL of DDW to 5 mL of 50 mg/mL MD-Hex-silane with 5 μL of the DPBA solution. A sample of the emulsion was taken (50 μL) and dispersed in 50 mL water (w/o/w emulsion) to create microparticles. Of the resulting suspension a sample was taken and viewed with SEM, and is shown in FIG. 2. The sample fully dissolved upon adding chloroform.

EXAMPLE 7

Microparticle Formation Using Siloxy Ether Derivatized Hydrophobic Maltodextrin and Various Additives A solution of MD-Hex-silane (polymer D in Table 1: 56 kDa, DS hex 1.5, DS silane 0.04 (theor.)) at 10% w/w polymer in dichloromethane was prepared. The MD-Hex-silane in an amount of 1 mL was poured into 15 mL of a solution of PVA 2% (w/w) that was saturated with DCM. The mixture was then homogenized for 1 min using a homogenizer (Silverson, 5100 rpm), and then immediately poured in 150 mL of DDW and stirred for 30 min. Particles were isolated by centrifugation (2000 rpm, 30 min.) and lyophilized thoroughly. SEM scanning showed smooth particles. Better yield and particles were obtained with MD-Hex-silane compared to MD-Hex at similar concentrations.

Lysozyme was spray-dried on a Buchi spray drier (Buchi, Switzerland) using a solution with 70% w/w protein and 30% w/w trehalose. Microparticle formation was repeated using MD-Hex-silane but with the addition of spray-dried lysozyme particles to the polymer solution at 10% or 20% (w/w—solids vs. polymer; 10.8 mg and 23.8 mg respectively).

Figure 3:
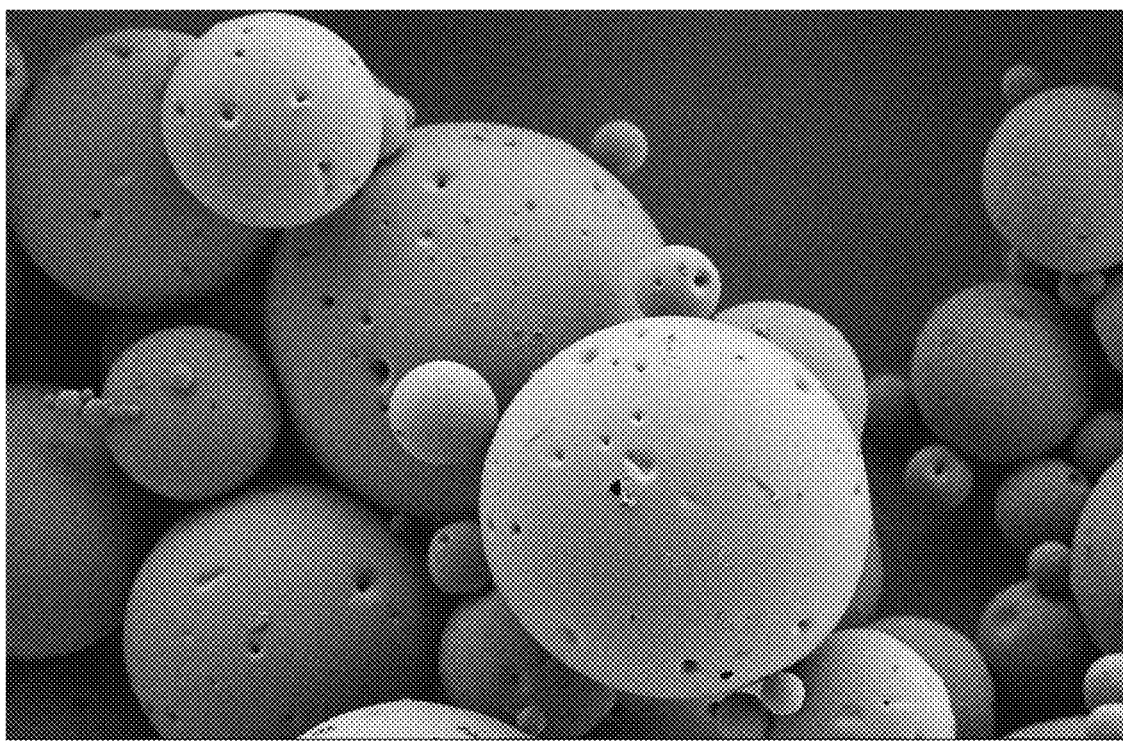
FIG. 3 is a micrograph of microparticles formed using the silyl ether-modified hydrophobic α(1→4)glucopyranose polymer with a lysozyme particle core.

FIG. 3 is a SEM image of microparticles formed according to this method.

What is claimed is:

1. An emulsion comprising a hydrophobic polymer, an arylboronic acid, a continuous phase, and a discontinuous phase, wherein the hydrophobic polymer is in the discontinuous phase and the arylboronic acid is in the continuous phase.

2. The emulsion of claim 1 wherein the arylboronic acid comprises a halogenated arylboronic acid.

3. The emulsion of claim 2 wherein the halogenated arylboronic acid comprises a phenyl group, a boronic acid group, and at least one halogen atom, wherein the boronic acid group and the at least one halogen atom are attached to the phenyl group at positions on the phenyl ring.

4. The emulsion of claim 2 wherein the halogenated arylboronic acid is according to Formula I:

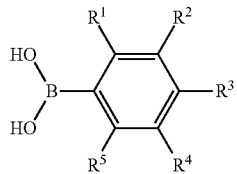

wherein one or more of $R^1$, $R^2$, $R^3$, $R^4$, and/or $R^5$ is selected from a halogen atom, and any $R^1$, $R^2$, $R^3$, $R^4$, and/or $R^5$ positions not occupied by a halogen atom are H.

5. The emulsion of claim 4 wherein the two of $R^1$, $R^2$, $R^3$, $R^4$, and $R^5$ are independently selected from halogen atoms.

6. The emulsion of claim 4 wherein the one or more of $R^1$, $R^2$, $R^3$, $R^4$, and/or $R^5$ are Cl.

7. The emulsion of claim 6 wherein $R^2$ and $R^4$ are Cl.

8. The emulsion of claim 2 comprising 3,5-dichlorophenylboronic acid.

9. The emulsion of claim 1 wherein the hydrophobic polymer comprises a degradable portion.

10. The emulsion of claim 1 wherein the hydrophobic polymer comprises a polysaccharide portion.

11. The emulsion of claim 10 wherein polysaccharide portion comprises poly-α(1→4)glucopyranose.

12. The emulsion of claim 1 wherein the hydrophobic polymer comprises a polymer backbone and a reactive group pendent from the polymer backbone.

13. The emulsion of claim 12 wherein the reactive group comprises a silyl ether group.

14. The emulsion of claim 1 wherein the hydrophobic polymer comprises a polymer backbone and a pendent group on the polymer backbone, the pendent group comprising a hydrocarbon group and a linker group between the hydrocarbon group and the polymer backbone, wherein the linker group comprises a silyl ether group.

15. The emulsion of claim 1 wherein the hydrophobic polymer is present at a concentration in the range of 0.005% wt to 5% wt.

16. The emulsion of claim 1 wherein the arylboronic acid is present at a concentration in the range of 0.005% wt to 5% wt.

17. The emulsion of claim 1 comprising a water-in-oil-in-water emulsion.

18. The emulsion of claim 1 further comprising a bioactive agent.

19. The emulsion of claim 1 comprising microparticulates comprising the hydrophobic polymer.

20. The emulsion of claim 19 wherein the microparticulates comprise a core comprising bioactive agent and a shell comprising the hydrophobic polymer.

21. A method for preparing an injectable or implantable medical material or article comprising steps of (a) preparing an emulsion comprising a hydrophobic polymer, an arylboronic acid, a continuous phase, and a discontinuous phase, wherein the hydrophobic polymer is in the discontinuous phase and the arylboronic acid is in the continuous phase, and wherein particulates comprising the hydrophobic polymer are formed in the emulsion, and (b) using the particulates for the preparation of, or as an injectable or implantable medical material or article.

22. The method of claim 21 wherein step (b) comprises forming the particulates into a medical implant.

23. Microparticles formed from a process comprising a step of preparing an emulsion comprising a hydrophobic polymer, an arylboronic acid, a continuous phase, and a discontinuous phase, wherein the hydrophobic polymer is in the discontinuous phase and the arylboronic acid is in the continuous phase, and wherein microparticles comprising the hydrophobic polymer are formed in the emulsion.

24. The emulsion of claim 1 wherein the continuous phase is an aqueous continuous phase.

25. The emulsion of claim 18 wherein the bioactive agent is selected from the group consisting of antibiotics, anti-coagulants, antihypertensive agents, anti-inflammatory agents, antiproliferatives, immunosuppressive agents, and steroids.

* * * * *

UNITED STATES PATENT AND TRADEMARK OFFICE
CERTIFICATE OF CORRECTION

| | |
|---|---|
| PATENT NO. | : 8,709,489 B2 |
| APPLICATION NO. | : 12/894983 |
| DATED | : April 29, 2014 |
| INVENTOR(S) | : Joram Slager, Aleksey V. Kurdyumov and Dale G. Swan |

It is certified that error appears in the above-identified patent and that said Letters Patent is hereby corrected as shown below:

In the Specification

<u>Column 26,</u>
Line 39, "of the had occurred" should be -- had occurred --

Signed and Sealed this
Thirty-first Day of March, 2015

Michelle K. Lee
*Director of the United States Patent and Trademark Office*